United States Patent [19]
Bloxsom et al.

[11] Patent Number: 5,460,030
[45] Date of Patent: Oct. 24, 1995

[54] METHOD AND TOOL FOR DETECTING AIR TRAPPED IN ENGINE COOLING SYSTEM

[75] Inventors: Thomas J. Bloxsom, Walled lake; Anthony H. Boden, Ann Arbor, both of Mich.

[73] Assignee: Ford Motor Company, Dearborn, Mich.

[21] Appl. No.: 193,973

[22] Filed: Feb. 9, 1994

[51] Int. Cl.$^6$ .............................. G01F 17/00; G01N 7/00
[52] U.S. Cl. ...................... 73/19.05; 73/19.1; 73/49.7; 73/149
[58] Field of Search .................. 73/19.05, 19.1, 73/37, 37.5, 39, 49.7, 118.1, 149

[56] References Cited

U.S. PATENT DOCUMENTS

| | | | |
|---|---|---|---|
| 3,911,256 | 10/1975 | Jones | 73/61.44 |
| 4,102,178 | 7/1978 | Mercik, Jr, et al. | 73/49.7 |
| 4,329,869 | 5/1982 | Toda | 73/19.1 |
| 4,700,561 | 10/1987 | Dougherty | 73/19.05 |
| 4,705,459 | 11/1987 | Buisine et al. | 417/53 |
| 4,763,518 | 8/1988 | Daviaud et al. | 73/149 |
| 4,862,729 | 9/1989 | Toda et al. | 73/19.05 |
| 5,235,971 | 8/1993 | Falb et al. | 128/203.14 |

OTHER PUBLICATIONS

Honeyman et al. "Air-In-Oil-Available Measurement Methods" The BFPR Jounal, pp. 275–281, 11, 1978.

*Primary Examiner*—Hezron E. Williams
*Assistant Examiner*—Michael J. Brock
*Attorney, Agent, or Firm*—David B. Kelley; Roger L. May

[57] ABSTRACT

A method for detecting trapped air in an engine cooling system includes the steps of delivering a volume of test air under pressure to the radiator of the cooling system, measuring the volume of test air delivered, measuring the pressure of test air delivered, and calculating the volume of trapped air in the cooling system using Boyle's law and the measured volume and pressure of test air. A device for carrying out the method comprises a pump for delivering test air to the radiator, a motor for driving the pump, a pressure gauge or pressure switch for sensing the pressure of test air delivered, and means for determining the volume of test air delivered.

6 Claims, 2 Drawing Sheets

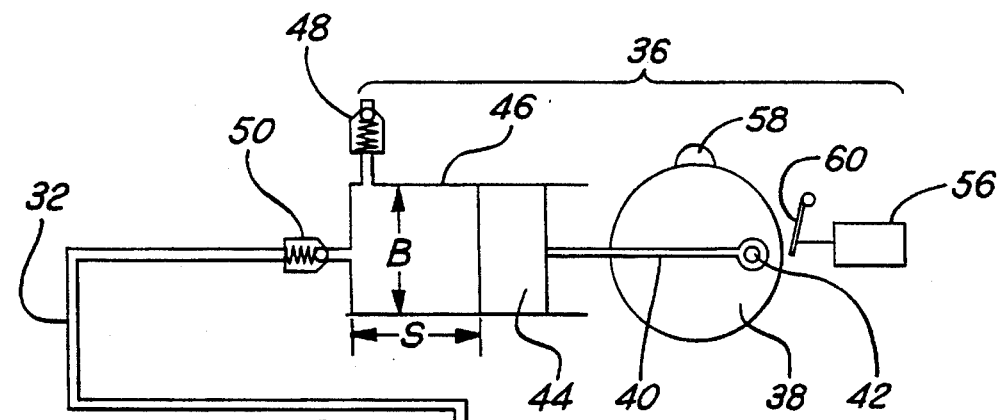
FIG. 5
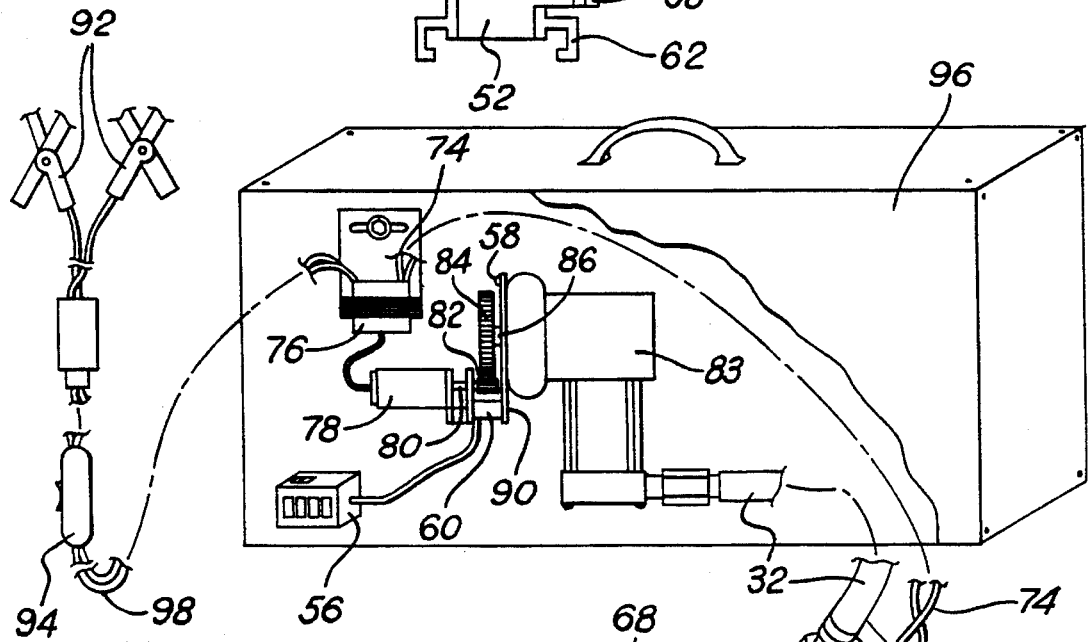
FIG. 6
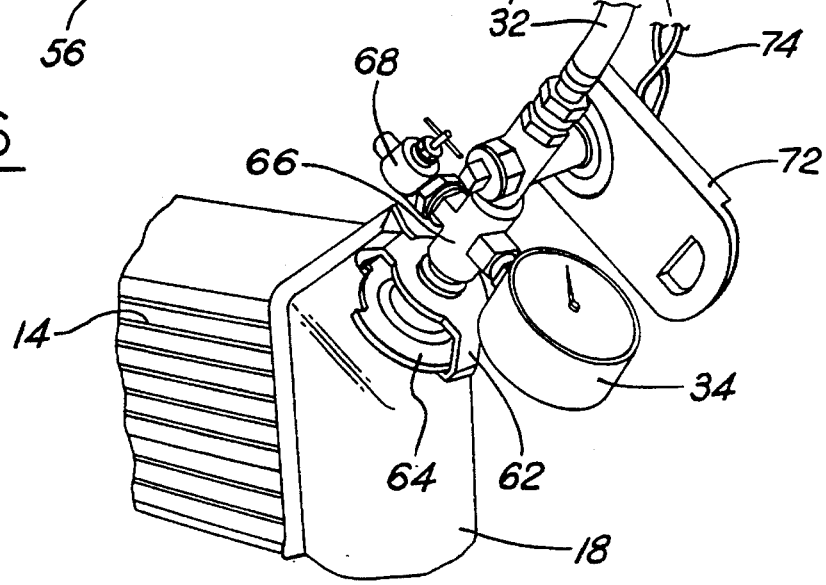

5,460,030

METHOD AND TOOL FOR DETECTING AIR TRAPPED IN ENGINE COOLING SYSTEM

FIELD OF THE INVENTION

The present invention relates to internal combustion engine cooling systems, and more particularly, to a method and tool for detecting air trapped in the cooling system of an engine.

BACKGROUND OF THE INVENTION

Internal combustion engines produce waste heat energy in addition to the mechanical energy generated to propel a vehicle. If the excess heat energy is removed, the engine block could overheat and crack, or otherwise break, necessitating expensive repairs. In many engines, an liquid cooling system removes the unwanted heat by providing a network of passages and conduits in the engine block through which liquid coolant circulates. The coolant then passes through a multi-finned radiator over which ambient air flows, extracting the heat.

Unwanted air can be introduced into the cooling system when it is being filled with coolant, for example, following repairs at a service station. The air may accumulate and form bubbles which can become trapped at various locations in the cooling system even though the coolant level appears to indicate that the cooling system is full. Unless the trapped air is removed, coolant flow can be reduced perhaps causing the engine to overheat, or can cause insufficient heater and defroster performance.

As a precautionary measure following filling of an automotive cooling system, current practice is to run the engine for a period of time to circulate the coolant in the system, with the cooling system fill/pressure cap removed, so that trapped air can escape. This procedure is time consuming, however, and essentially assumes that all trapped air will circulate past the open filler neck and escape after a certain length of time. If the volume of trapped air in the cooling system could be determined, the time an engine would have to be run to expel that air could be more accurately estimated, thus saving time and expense.

One method of determining whether air is trapped in the cooling system is shown in FIG. 7. Cooling system 112 is filled with coolant 114. A radiator 116 is connected to cooling system 112 by hoses 118. An air bubble 120 trapped in the cooling system can be detected, if large enough, when the level 122 of coolant in a pressure vessel 124, which is attached to the radiator filler neck 126, decreases upon pressurization of the air above level 122 by pump 128. However, this method is adversely affected by temperature changes and coolant level in pressure vessel 124. In addition, the device is heavy, bulky, and difficult to set up or to move easily, particularly when used in close quarters under the hood of an engine.

SUMMARY OF THE INVENTION

The present invention provides an advantageous method and device for detecting air trapped in the cooling system of an engine so that the engine will not need to be run for an excessive period of time to expel any trapped air, and which avoids the drawbacks of the prior methods discussed above. A method for determining the volume of trapped air in an internal combustion engine cooling system includes the steps of delivering a volume of test air under pressure to the cooling system, measuring the volume of test air delivered to the cooling system, measuring the pressure of the test air in the cooling system, and calculating the volume of air trapped in cooling system using Boyle's Law and the measured volume and pressure of the test air.

A device for determining the volume of trapped air in the automotive cooling system comprises means for attachment to the cooling system, means for delivering a volume of test air under pressure to the cooling system connected to the means for attachment, means for determining the volume of test air delivered to the cooling system by the means for delivering air, and means for determining the pressure of the test air delivered to said cooling system. Preferably, the means for delivering the test air comprises a positive displacement pump with a counter attached thereto for counting the number of cycles of a piston within the positive displacement pump so that the volume of the test air can be measured by multiplying the number of cycles recorded by the counter by the working volume of the positive displacement pump as calculated by the bore and stroke size of the pump. The means for determining the volume of the test air can also be an air flow meter.

The means for determining pressure of the test air after delivered to the radiator is a pressure gauge, or, preferably, a pressure switch which turns off the means for delivering test air when the pressure of the test air reaches a pre-set pressure.

Thus, an object of the present invention is to provide a method and device for detecting the volume of air trapped in an engine cooling system after the system is filled with coolant.

Another object is to provide a method and device which can be used to determine when an engine has idled sufficiently to allow air trapped in the cooling system to escape through an uncapped radiator filler neck.

A further object of the present invention is to provide an inexpensive device for quickly and easily detecting the volume of air trapped in an engine cooling system.

Yet another object of the present invention is to provide a method and tool for verifying the integrity of the cooling system during the engine cooling system design phase.

A further object is to provide a method and tool for auditing vehicle cooling systems to ensure proper fill level prior to shipment and sale of the vehicle.

BRIEF DESCRIPTION OF THE DRAWINGS

FIG. 5 is a schematic diagram of the preferred embodiment of the trapped air detection device of the present invention.

FIG. 6 is a perspective view of the trapped air detection device of the present invention shown attached to the radiator of an engine cooling system.

DETAILED DESCRIPTION OF THE PREFERRED EMBODIMENTS

Figure 1:
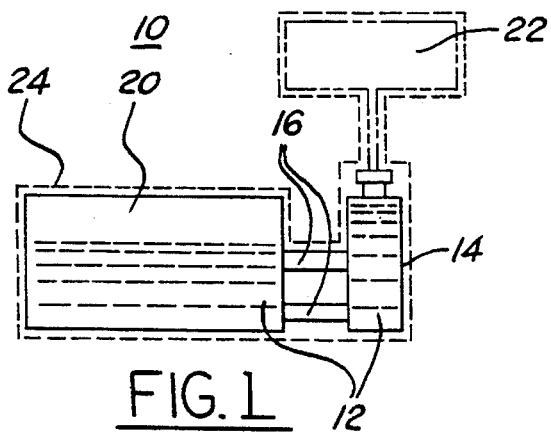
FIG. 1 is a schematic diagram of an engine cooling system having air trapped within and showing a volume of test air which will be added to the cooling system radiator under pressure according to the method of the present invention.
Figure 2:
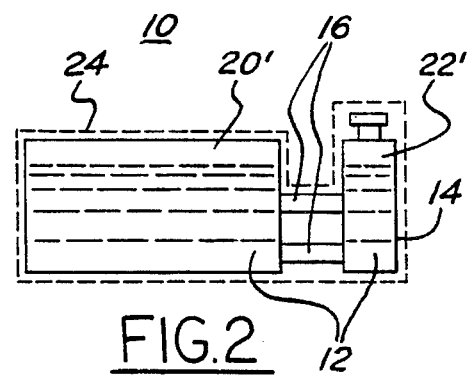
FIG. 2 is a schematic diagram of an engine cooling system shown after a volume of test air has been added to the radiator under pressure according to the method of the present invention.

FIGS. 1 and 2 show conceptually the method of the present invention. In FIG. 1, an engine cooling system 10 is filled with coolant 12. A radiator 14 is connected to cooling system 10 by hoses 16. Radiator 14 has filler neck 18 which allows coolant to enter cooling system 10 upon filling, for example, after repairs at a service station. If air is introduced into cooling system 10 upon filling, such air may become trapped as bubbles at various locations in cooling system 10. Trapped air bubble 20 collectively represents these air bubbles introduced into cooling system 10 (FIG. 1). In the method of the present invention, a known volume of test air 22 is added to radiator 14 of cooling system 10 through filler neck 18 thus compressing trapped air 20. When the pressure of test air 22' and volume of test air 22 are measured (FIGS. 1 and 2), the volume of trapped air 20 can be calculated using Boyles's law as further described below.

Boyle's law, which is a special case of the ideal gas law with the temperature and mass of a control volume held constant, gives the relationship between pressure and volume as follows:

$$P_i * V_i = P_f * V_f$$

where $P_i$=Initial pressure of the control volume;

$V_i$=Initial volume of the control volume;

$P_f$=Final pressure of the control volume; and $V_f$=Final volume of the control volume.

In the cooling system of FIGS. 1 and 2, the control volume 24 includes trapped air 20, coolant 12, and test air 22. $P_i$ is nominally atmospheric pressure, and $V_i$ is the sum of the volumes of trapped air 20, $V_{20}$, and test air 22, $V_{22}$. Thus, $$P_i * (V_{20} + V_{22}) = P_f * V_f$$

After test air 22 has been compressed into radiator 14 as shown in FIG. 2, the pressure of control volume 24 rises to $P_f$. However, since the volume of cooling system 10 containing coolant 12 and air, either trapped or test, remains essentially constant, and since coolant 12 is incompressible and thus occupies the same volume before and after test air is compressed into radiator 14, the final volume $V_f$ of air, both trapped and test, in control volume 24 (FIG. 2) equals the volume $V_{20}$ of trapped air 20 before test air 22 is compressed into radiator 14 (FIG. 1). As such, $$P_i * (V_{20} + V_{22}) = P_f * V_{20}$$

Solving for $V_{20}$, the volume of trapped air 20 in cooling system 10, yields $$V_{20} = \frac{P_i * V_{22}}{(P_f - P_i)}.$$

With this equation, the volume of trapped air 20 in cooling system 10 can be calculated by measuring the final pressure $P_f$ and the volume of test air $V_{22}$ added to cooling system 10 at initial pressure $P_i$, typically atmospheric pressure.

Figure 3:
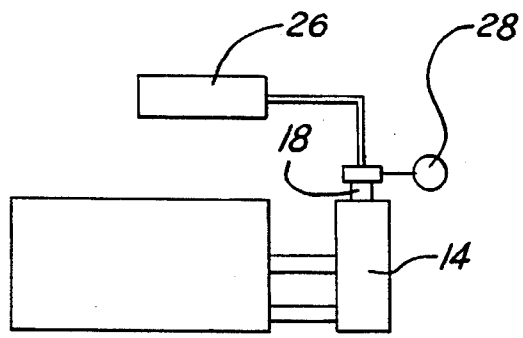
FIG. 3 is a schematic diagram of an engine cooling system having a device for detecting trapped air in the cooling system according to the present invention attached to the radiator, including means for delivering air under pressure and means for sensing pressure within the radiator.

FIG. 3 depicts schematically a means for delivering air 26 connected to radiator 14 which is capable of delivering a volume of test air 22 under pressure to cooling system 10. The means for delivering air 26 can be any of a number of mechanisms for delivering air under pressure, such as a positive displacement pump, an air compressor, an air flow meter, or other air pumping devices known to those skilled in the art and suggested by this disclosure. The final pressure, $P_f$, of the test air 22 delivered to cooling system 10 is sensed by means for sensing 28, attached near filler neck 18, which can be, for example, a pressure gauge or a pressure switch or other pressure sensing devices known to those skilled in the art (FIG. 3).

Figure 4:
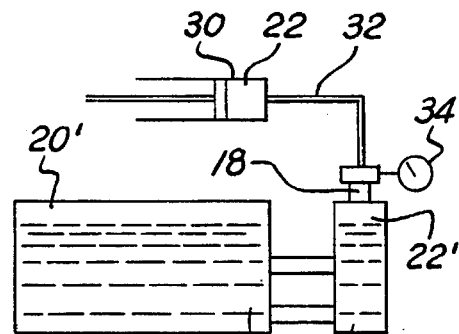
FIG. 4 is a schematic diagram of the trapped air detecting device of the present invention similar to FIG. 3 and showing a piston operated air volume gauge and a pressure gauge connected to the radiator filler neck.
Figure 7:
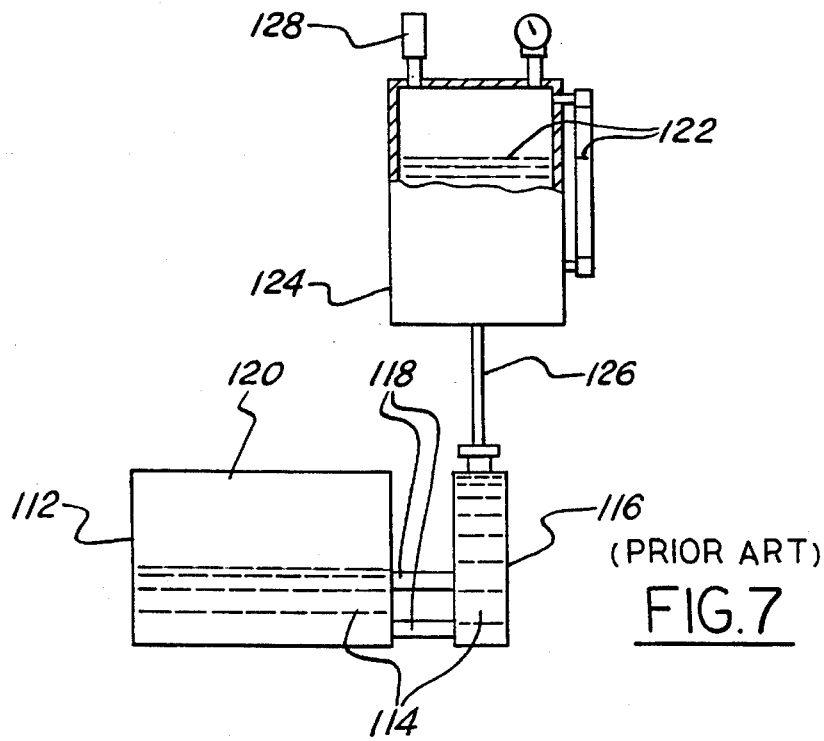
FIG. 7 is a schematic view of a prior art method for detecting trapped air in an engine cooling system.

A schematic of a set-up for measuring the desired volume of test air 22, $V_{22}$, and final pressure, $P_f$, is shown in FIG. 4. An air volume gauge 30 delivers a known volume of test air 22 to radiator 14 through air hose 32 and filler neck 18. Pressure gauge 34, attached to filler neck 18, measures the pressure of test air 22' delivered to radiator 14 by air volume gauge 30.

A more detailed schematic of a device for delivering test air 22 to radiator 14 of cooling system 10 is shown in FIG. 5. Air delivery is accomplished by means of positive displacement pump 36. Flywheel 38 is attached to the shaft (not shown) of a motor (not shown) for rotation. Connecting rod 40 attaches piston 44 to flywheel 38 at a radially outer position 42 in a known manner so as to convert rotational movement of flywheel 38 to translational movement of piston 44. Piston 44 has a stroke length S within cylinder 46, which has bore B.

Still referring to FIG. 5, a pair of valves at the end of cylinder 46 opposite flywheel 38 controls air movement through pump 36. Intake valve 48 opens on the intake stroke, that is, movement of piston 44 toward flywheel 38, to allow air, typically at atmospheric pressure, to enter cylinder 46. Exhaust valve 50 simultaneously shuts as vacuum pressure builds in cylinder 46. After piston 44 has reached a maximum length of travel toward flywheel 38 and cylinder 46 is filled with air, the exhaust cycle begins. Pressure in cylinder 46, which builds as piston 44 moves away from flywheel 38, shuts intake valve 48 to prevent air from exiting through intake valve 48 and opens exhaust valve 50 to allow the air in cylinder 46 to pass into air hose 32. After piston 44 has travelled a stroke S length away from flywheel 38, the intake-exhaust cycle just described begins again. Intake valve 48 and exhaust valve 50 are preferably one-way check valves, such as Reed valves, or other such valves known in the art.

Each cycle of piston 44 delivers a volume $V_{cylinder}$ of air through air hose 32 to interior space 52 of radiator connector 54 (FIG. 5). The volume $V_{cylinder}$ is calculated using the volume equation for a cylinder and the stroke S and bore B dimensions of pump 36 as follows:

$$V_{cylinder} = \pi/4 * B^2 * S$$

The number of cycles of piston 44 is recorded by counter 56. Cam 58 on flywheel 38 completes one cycle for each cycle of piston 44 within cylinder 46. As cam 58 rotates and depresses switch 60, switch 60 causes the number on counter 56 to increase by one in a known fashion. After air has been pumped into radiator 14, the number of cycles N of piston 44 is read from counter 56 and multiplied by the cylinder volume $V_{cylinder}$ to determine the volume $V_{22}$ of test air 22. Thus, $$V_{22} = V_{cylinder} * N = \pi/4 * B^2 * S * N$$

Pressure gauge 34 then shows the final pressure $P_f$ of test air 22 in radiator 14. The volume $V_{20}$ of trapped air 20 in cooling system 10 can then be calculated as follows:

$$V_{20} = \frac{P_i * (\pi/4 * B^2 * S * N)}{(P_f - P_i)}.$$

A perspective view of a preferred embodiment of a device for detecting trapped air in a cooling system is shown in FIG. 6. Clamp 62 fits onto radiator filler cap receiving plate 64 in a fashion similar to a conventional radiator cap. T-joint 66 connects filler neck 18, pressure release valve 68, pressure gauge 34, and air hose 32. When opened, pressure release valve allows pressurized test air 22' (FIG. 2) to exhaust from filler neck 18. A pressure relief valve 70 (FIG. 5) can be installed to protect against system overpressurization.

Referring again to FIG. 6, pressure switch 72 is connected to T-joint 66, and is also connected electrically via pressure switch wires 74 to relay 76. Relay 76 shuts off motor 78 when air pressure as sensed by pressure switch 72 reaches a pre-set limit. Motor 78, preferably a dc motor, drives shaft 80 upon which shaft gear 82 is mounted. Shaft gear 82 meshes with gear 84, which is mounted on flywheel shaft 86. Flywheel shaft 86 extends into flywheel housing 88 and connects with flywheel 38 and drives piston 44 to pump air from cylinder 46 to air hose 32, as described above (FIG. 5).

As seen in FIG. 6, cam 58 is mounted on a side of disk 90 facing flywheel gear 84 for rotation therewith such that cam 58 contacts switch 60 on each revolution of flywheel shaft 86. Switch 60 transmits each contact by cam 58 to counter 56 which records the number of piston 44 cycles for use in calculating the volume of air delivered to radiator 14.

Power is delivered to motor 78 through relay 76 from an electrical source, such as vehicle battery (not shown). Battery clamps 92 connect to the battery terminals (not shown), and power switch 94 provides a means for switching the device on or off. Alternatively, a conventional cigarette lighter adapter (not shown) may be used to connect the device to a power source, which, in this case, would again be the vehicle battery. Alternating current (a.c.) can also be used to provide power to motor 78 for driving pump 36, with the understanding that motor 78 would be an a.c. driven motor. Relay 76, motor 78, pump 36 and counter 56 are preferably contained in case 96 through which extends air hose 32, pressure switch wires 74 and power wires 98.

With the method and device just described, the volume of air trapped in a vehicle cooling system may be quickly, easily, and accurately calculated so that a suitable engine idle time after refilling is allowed.

Although the preferred embodiments of the present invention have been disclosed, various changes and modifications may be made without departing from the scope of the invention as set forth in the appended claims.

We claim:

1. A method for determining the volume of trapped air in an internal combustion engine cooling system including the steps of:

delivering a volume of test air under pressure to said cooling system using a piston operated pump;

measuring said volume of test air delivered to said cooling system by reading the number of cycles of a piston in said pump recorded by a counter connected to said pump and multiplying said number of cycles by the working volume of said pump;

measuring the pressure of said test air in said cooling system; and calculating the volume of said trapped air in said cooling system using the measured volume and pressure of said test air in Boyle's law.

2. The method according to claim 1, wherein said pressure of said test air is determined using a pressure gauge.

3. The method according to claim 1, wherein said pressure of said test air is determined using a pressure switch attached to said cooling system wherein said pressure switch turns off said positive displacement pump when the pressure of said test air reaches a pre-set pressure.

4. A device for detecting trapped air in an automotive cooling system, the device comprising:

a positive displacement pump for delivering a volume of test air under pressure to said cooling system;

a counter attached to said positive displacement pump for counting the number of cycles of a piston within said positive displacement pump so that the volume of said test air can be measured by multiplying the number of cycles recorded by said counter by the working volume of said positive displacement pump as calculated by the bore and stroke size of said pump; and means for sensing the pressure of said test air delivered to said cooling system.

5. A device according to claim 4, wherein said means for determining said pressure of said test air is a pressure gauge.

6. A device according to claim 4, wherein said means for determining said pressure of said test air is a pressure switch which turns off said means for delivering said test air when the pressure of said test air reaches a pre-set pressure.

* * * * *